(12) United States Patent
Cummins

(10) Patent No.: US 9,820,877 B2
(45) Date of Patent: Nov. 21, 2017

(54) WEDGE HOLDING MECHANISM FOR VASCULAR INTERVENTION DEVICE DELIVERY SYSTEM

(71) Applicant: Cook Medical Technologies LLC, Bloomington, IN (US)

(72) Inventor: Sean Cummins, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 257 days.

(21) Appl. No.: 14/748,943

(22) Filed: Jun. 24, 2015

(65) Prior Publication Data

US 2016/0074190 A1    Mar. 17, 2016

Related U.S. Application Data

(60) Provisional application No. 62/050,266, filed on Sep. 15, 2014.

(51) Int. Cl.
*A61F 2/06* (2013.01)
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC ............ A61F 2002/0072; A61F 2/2466; A61F 2002/011; A61F 2/95; A61F 2002/9517; A61F 2/954; A61F 2/958; A61F 2002/9583; A61F 2002/9586; A61F 2/962; A61F 2/966; A61F 2002/9665; A61F 2/97

See application file for complete search history.

(56) References Cited

U.S. PATENT DOCUMENTS

| | | |
|---|---|---|
| 6,190,360 B1 | 2/2001 | Iancea et al. |
| 6,238,402 B1 | 5/2001 | Sullivan, III et al. |
| 7,967,829 B2 | 6/2011 | Gunderson et al. |
| 7,976,574 B2 | 7/2011 | Papp |
| 8,500,789 B2 | 8/2013 | Wuebbeling et al. |
| 2005/0273151 A1 | 12/2005 | Fulkerson et al. |
| 2007/0032860 A1 | 2/2007 | Brooks et al. |
| 2007/0055342 A1 | 3/2007 | Wu et al. |
| 2007/0088421 A1 | 4/2007 | Loewen |
| 2007/0156225 A1 | 7/2007 | George et al. |
| 2007/0168014 A1 | 7/2007 | Jimenez et al. |

(Continued)

*Primary Examiner* — Jonathan Miles
(74) *Attorney, Agent, or Firm* — Liell & McNeil

(57) ABSTRACT

A vascular intervention device delivery system, such as for implanting a self expanding stent, includes a thumbwheel rotatably mounted in a handle. The thumbwheel includes a radially outward thumb surface. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. A holding mechanism is operably positioned between the handle and the thumbwheel, and includes a wedge pin trapped to move in a wedge shaped cavity between a wedged position that prevents the thumb wheel from rotating, and an unwedged position that permits the thumbwheel to rotate to facilitate deployment of a self-expanding stent.

20 Claims, 3 Drawing Sheets

(56) References Cited

U.S. PATENT DOCUMENTS

| | | |
|---|---|---|
| 2008/0091257 A1 | 4/2008 | Andreas et al. |
| 2009/0210046 A1 | 8/2009 | Shumer et al. |
| 2012/0041537 A1 | 2/2012 | Parker et al. |
| 2012/0101562 A1 | 4/2012 | Gunderson et al. |
| 2012/0123516 A1 | 5/2012 | Gerdts et al. |
| 2012/0158120 A1 | 6/2012 | Hacker et al. |
| 2012/0330401 A1 | 12/2012 | Sugimoto et al. |
| 2013/0013047 A1 | 1/2013 | Ramos et al. |
| 2013/0018451 A1 | 1/2013 | Grabowski et al. |
| 2013/0110223 A1 | 5/2013 | Munsinger et al. |
| 2013/0304187 A1* | 11/2013 | Yamashita .............. A61F 2/966 623/1.12 |

* cited by examiner

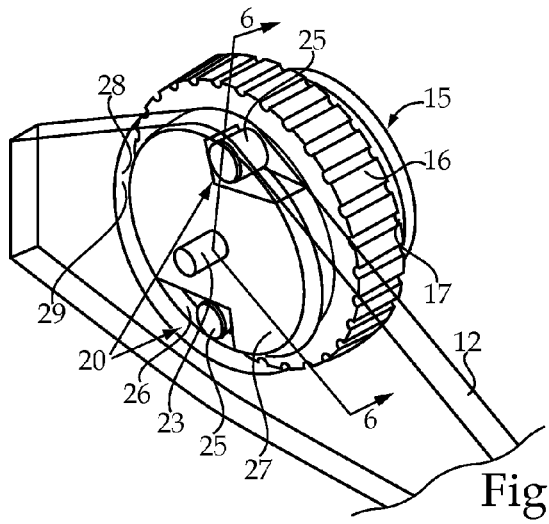
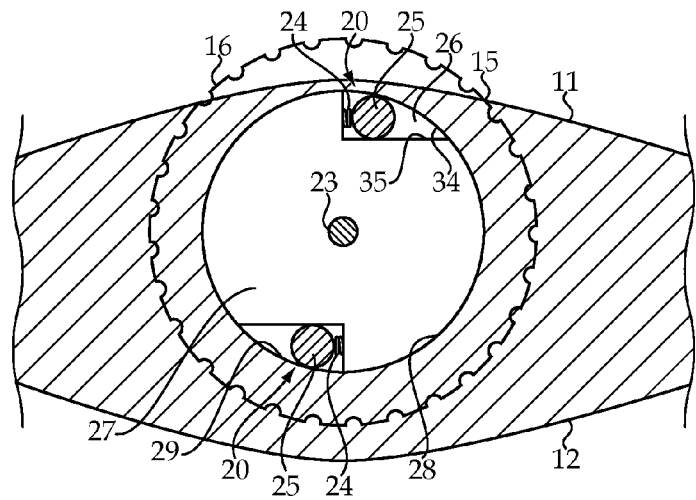
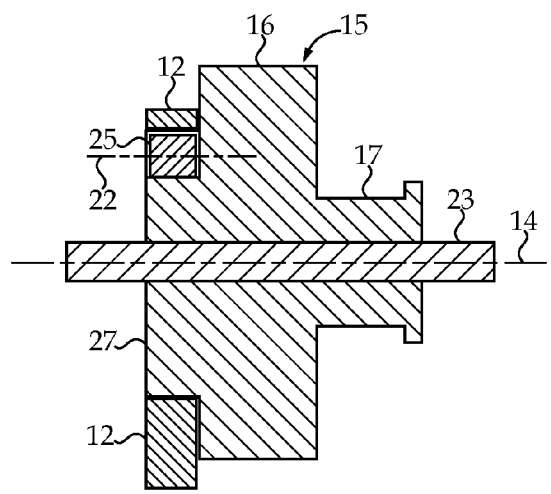

WEDGE HOLDING MECHANISM FOR VASCULAR INTERVENTION DEVICE DELIVERY SYSTEM

TECHNICAL FIELD

The present disclosure relates generally to vascular intervention device delivery systems, and more particularly to a feature that holds the thumbwheel against rotation in one direction, but permits rotation in an opposite direction for deployment of a vascular intervention device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficulty maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent.

The present disclosure is directed toward one or more of the problems set forth above.

SUMMARY OF THE DISCLOSURE

In one aspect, a vascular intervention device delivery system includes a thumbwheel rotatably mounted in a handle and having a radially outward thumb surface. A holding mechanism is operably positioned between the handle and the thumbwheel, and includes a wedge pin trapped to move in a wedge shaped cavity between a wedged position that prevents the thumbwheel from rotating with respect to the handle in a forward direction, and an unwedged position that permits the thumbwheel to rotate with respect to the handle in a reverse direction. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. The retractable sheath moves responsive to rotation of the thumbwheel in the reverse direction.

In another aspect, a method of operating the vascular intervention device delivery system includes rotating the thumbwheel in the reverse direction to build up tension in the retractable sheath and pull without moving the retractable sheath relative to the distal carrier segment of the catheter. A portion, which is less than all, of the distal carrier segment is uncovered by continuing to rotate the thumbwheel in the reverse direction. Rotation of the thumbwheel in the reverse direction is paused. Tension in the pull and the retractable sheath are maintained by moving the wedge pin of the holding mechanism to the wedged position and preventing rotation of the thumbwheel in the forward direction. A remaining portion of the distal carrier segment is uncovered by resuming rotation of the thumbwheel in the reverse direction and moving the wedge pin of the holding mechanism to the unwedged position.

BRIEF DESCRIPTION OF THE DRAWINGS

FIG. 4 is a perspective partially transparent view of an assembly plate for the handle shown in FIG. 1;

FIG. 5 is a partial sectioned side view showing the holding mechanism according to the present disclosure;

FIG. 6 is a sectioned side view through the thumbwheel of FIGS. 1, 4 and 5 as viewed along section lines 6-6 of FIG. 4;

DETAILED DESCRIPTION

Figure 1:
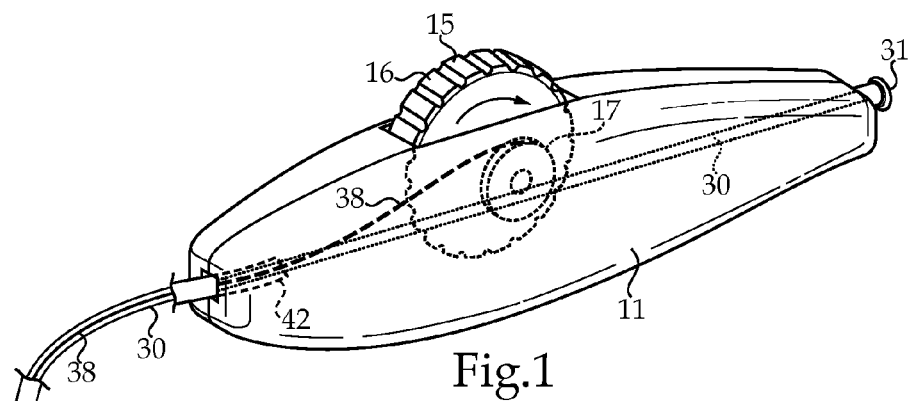
FIG. 1 is a perspective schematic view of a vascular intervention device delivery system according to the present disclosure.
Figure 2:
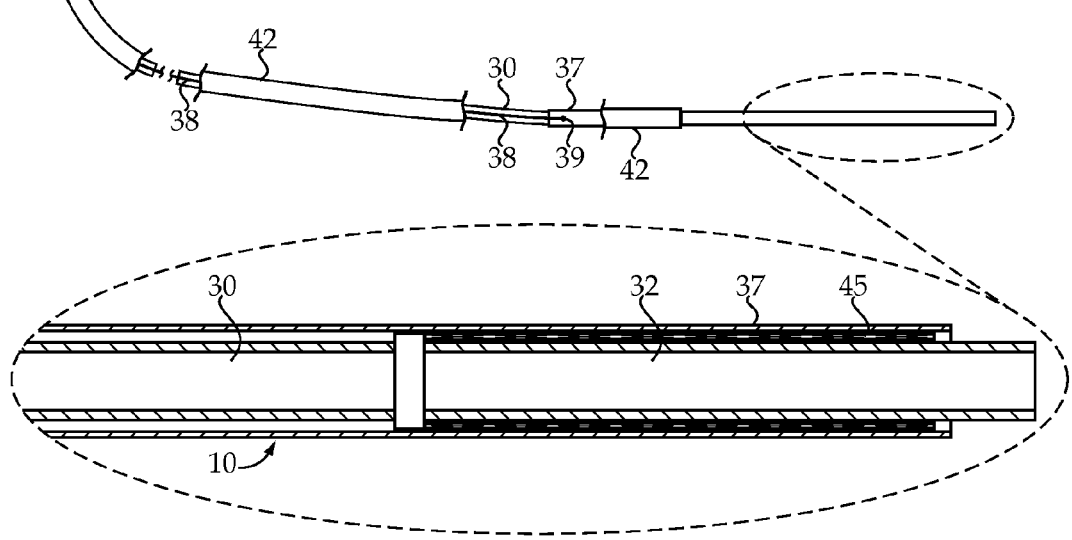
FIG. 2 is an enlarged view of the distal segment of the delivery system shown outlined with a dashed line in FIG. 1.
Figure 3:
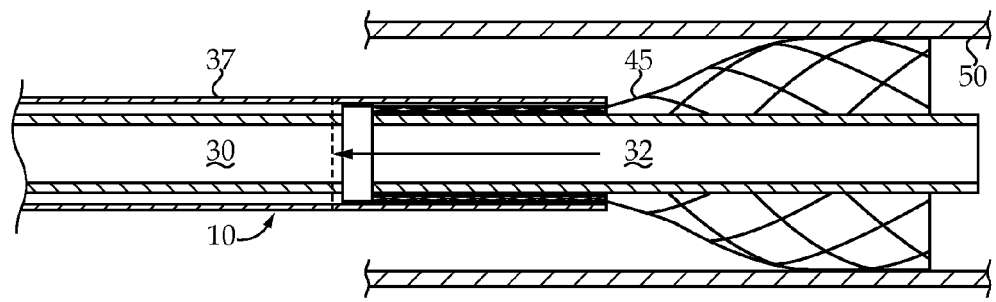
FIG. 3 is a view similar to FIG. 2 about half way through a deployment of a self expanding stent.

Referring to FIGS. 1-3, a vascular intervention device delivery system 10 is shown before and during delivery of a self expanding stent 45 into the vessel 50 of a patient. Delivery system 10 includes a handle 11 that may be gripped in one hand by a user during a delivery procedure. Handle 11 may, for instance, be manufactured from a suitable molded plastic, such as in two longitudinal halves that are joined in any suitable manner to form the complete handle 11. A thumbwheel 15 is rotatably mounted on an axle 23 in the handle 11 and has a radially outward thumb surface 15 and a spool 17. A catheter 30 has a proximal end 31 attached to handle 11, and a distal carrier segment 32 for mounting a vascular intervention device, such as a self expanding stent 45, thereon. Proximal end 31 may take the form a Luer lock fitting so that treatment fluids or the like may be injected through catheter 30 in a manner well known in the art. A retractable sheath 37 is movable with respect to catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art. In most versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal.

A wire retention/stability sheath 42 surrounds a majority of the length of pull 38, and serves to keep pull 38 in close proximity to the outer surface of catheter 30 over much of the length of delivery system 10. Wire retention/stability sheath 42 may be unattached to catheter 30, pull 38 or retractable sheath 37, but may be attached to move with pull 38 and/or retractable sheath 37. On the other hand, wire retention/stability sheath 42 may be attached to catheter 30 at one or more locations so that pull 38 and retractable sheath 37 also move with respect to wire retention/stability sheath 42 during the delivery process. Wire retention/stability sheath 42 may terminate at its proximal end at a fixation point within handle 11.

When in its pre-deployment configuration, as shown in FIGS. 1 and 2, a vascular intervention device, such as a self expanding stent 45, is disposed between an outer surface of the distal carrier segment 32 of catheter 30, and an inner surface of the retractable sheath 37. During a typical procedure, the distal carrier segment 32 is positioned at a treatment location within a vessel 50 of a patient. After achieving proper positioning, the user then grips handle 11 and begins to rotate thumbwheel 16 so that pull 38 is wound onto spool 17. As this occurs, pull 38 and retractable sheath 37 move proximally with respect to catheter 30 to allow the self expanding stent 45 to expand away from carrier segment 32 and into contact with the inner wall of vessel 50 in a manner well known in the art. During this process, catheter 30 is placed in compression while both pull 38 and retractable sheath 37 are in tension. According to the present disclosure, handle 11 and thumbwheel 15 include a structure that allows thumbwheel 15 to rotate to wind pull 38 onto spool 17, but prevent rotation in an opposite direction. This aspect of the disclosure allows the user to stop the deployment procedure while retaining the stored elastic energy in pull 38 and retractable sheath 37.

Referring now in addition to FIGS. 4-6, a holding mechanism 20 provides the structure that prevents thumbwheel 15 from rotating in a forward direction. In particular, handle 11 may be formed to include, or have attached to an inner surface, an assembly plate 12 that defines a wedge bore 28 that receives a wedge body 27 of thumbwheel 15. Together, the cylindrical surface 29 that defines wedge bore 28 and wedge body 27 define a wedge shaped cavity 26. In particular, the wedge shaped cavity includes a first curved wall 34 that converges with a planar wall 35. Holding mechanism 20 is operably positioned between the handle 11 and the thumbwheel 15, and includes a wedge pin 25 trapped to move in the wedge shaped cavity 26. Wedge pin 25 is movable between a wedged position that prevents the thumbwheel 15 from rotating with respect to handle 11 in the forward direction, and an unwedged position that permits the thumbwheel 15 to rotate with respect to the handle in the reverse direction.

Holding mechanism 20 may include a spring 24 that is operably positioned in wedge shaped cavity 26 to bias the wedge pin 25 toward the wedged position. Those skilled in the art will appreciate that spring 24 may be omitted without departing from the present disclosure. Wedge pin 24 may be constructed from any suitable material and have a stable rigid circular cross section, may include a smooth or roughened outer surface to better interact with walls 34 and 35, or may have some radial deformation capability in order to provide a better hold at the wedged position. Wedge pin 25 may tend to roll out of the wedged position when rotation of the thumbwheel is resumed in the reverse direction. Likewise, when rotation in reverse direction is stopped, the wedge pin 25 can roll from the unwedged position into the wedged position to prevent rotation of the thumbwheel in the forward direction.

When the thumbwheel 15 is rotated about axis 14, the wedge pin 25 may rotate about its own axis 22. In other words, wedge pin 25 may rotate about axis 22 in the wedge shaped cavity 26 responsive to rotation of the thumbwheel 15 in the reverse direction about axis 14. In addition, one could expect holding mechanism 20 to orbit axis 14 responsive to rotation of thumbwheel 15 in the reverse direction. In the illustrated embodiment, vascular intervention device delivery system 10 is shown as including two holding mechanisms 20 that are substantially identical but located on opposite sides of axis 14.

Figure 7:
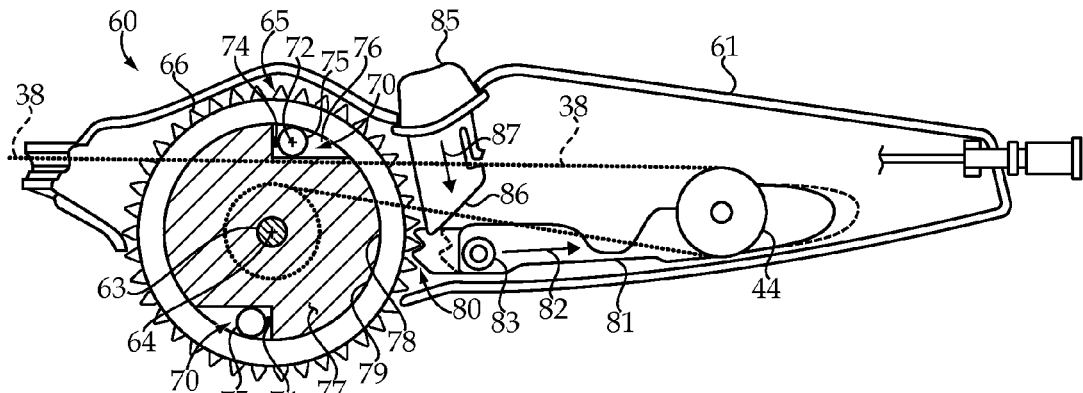
FIG. 7 is a sectioned side view of a handle portion of a vascular intervention device delivery system according to another aspect of the present disclosure.
Figure 8:
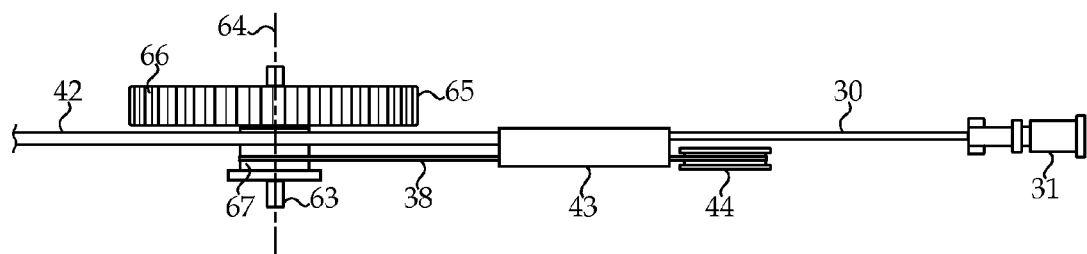
FIG. 8 is a top view of the inner workings of the vascular intervention device delivery system of FIG. 7, minus the handle.
Figure 9:
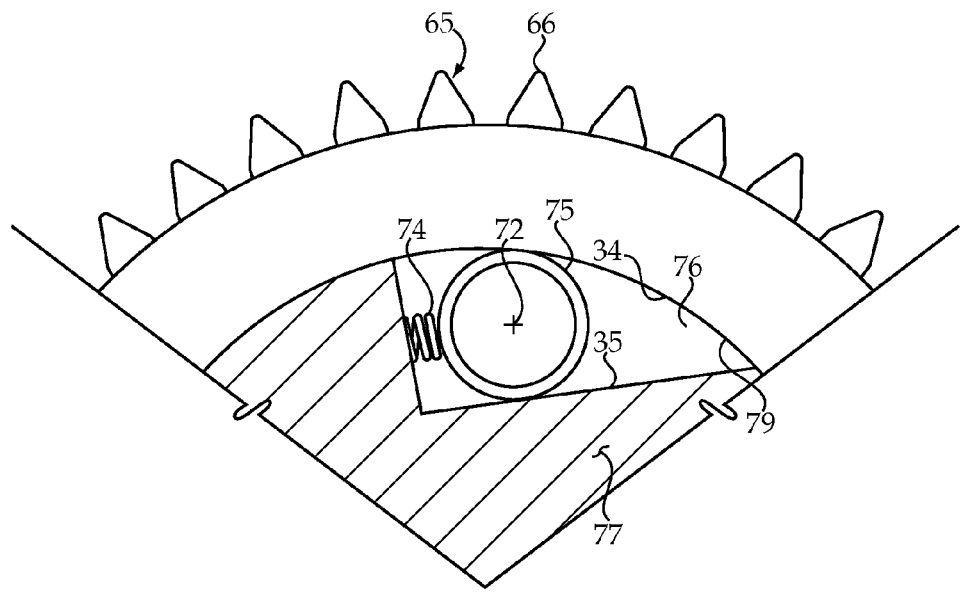
FIG. 9 is an enlarged side view of the holding mechanism for the vascular intervention device delivery system of FIG. 7.

Referring now to FIGS. 7-9, a vascular intervention device delivery system 60 according to another aspect includes a holding mechanism 70 and a handle 61 with a structure that differs from that shown in relation to FIGS. 4-6. One difference in this example is that curved wall 34 is a portion of a cylindrical surface 79 defined by thumbwheel 65. The curved wall 34 of the wedge shaped cavity 26 was defined by the assembly plate 12 in the embodiment of FIGS. 4-6. In addition, the version of FIGS. 7-9 differs in that the wedge body 77 is defined by the handle 61, whereas this feature was defined by the thumbwheel 15 in the case of the earlier embodiment. Thus, the holding mechanisms 70 shown in relation to the device delivery system 60 has a reverse construction of that shown in the earlier embodiment, but has an identical function. Thus, like the earlier embodiment, a spring 74 may be located in wedge shaped cavity 76 in order to bias wedge pin 75 from an unwedged position to a wedged position between curved wall 34 and planar wall 35. Handle 61, thumbwheel 65 and wedge pin 75 may all be formed from a suitable plastic material, or have a different material construction. For instance, wedge pin 75 may be metallic without departing from the intended scope of the present disclosure.

Vascular intervention device delivery system 60 includes a handle 61 within which assembly plate 12 as described earlier is mounted. Assembly plate 12 supports an axle 63 that defines a thumbwheel axis of rotation 64. Like the earlier embodiment, thumb wheel 65 includes both a radially outward thumb surface 66 and a spool 67. Pull 38 is wound upon spool 67 when the device delivery system 60 is operated. In this version, the wire retention/stability sheath 42 terminates at a junction box 43 (not shown in FIG. 7 for sake of clarity) positioned within handle 61. The pull 38 is positioned within the wire retention/stability sheath 42 until emerging from junction box 43 to turn direction around an idler wheel 44, and return in a reverse direction for being wound onto spool 67 as best shown in FIGS. 7 and 8.

Like the previous embodiment, holding mechanism 70 provides a structure that prevents thumbwheel 65 from rotating in a forward direction. Holding mechanism 70 permits a user to rotate thumbwheel 65 in a reverse direction via interaction between the users thumb and radially outward thumb surface 66 in a known manner. Thumbwheel 65 may be mounted to rotate on an axle 63 that defines the rotation axis 64. When thumbwheel 65 is rotated in the reverse direction, pull 38 may be wound onto a spool 67 in order to mover retractable sheath 37 proximally in order to uncover and deploy self expanding stent 45 as shown in FIGS. 1-3. Like the earlier embodiment, wedge pin 75 may rotate about its own axis 72 responsive to rotation of thumbwheel 65. In addition, the entire holding mechanism 70 may orbit axis 64 and axle 63 when thumbwheel 65 is being rotated in the reverse direction. Vascular intervention device delivery system 60 may include two holding mechanisms 70 located on opposites sides of axis 64. Nevertheless, those skilled in the art will appreciate that a vascular intervention device delivery system including one holding mechanism or three or more holding mechanisms would also fall within the intended scope of the present disclosure.

In addition to holding mechanism 70, vascular intervention device delivery system 60 includes a lock 80 that allows thumbwheel 65 to be disabled during shipment and during positioning of the distal carrier segment 32 (FIGS. 1-3) at a treatment location within a patient. The lock 80 is moveable between a locked position, as shown, and an unlocked position shown by dashed lines. The lock 80 includes a latch 81 positioned in handle 61 and moveable along a line 82 between the locked position at which the latch 81 engages the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a slanted surface 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site.

The vascular intervention device delivery system 10, 60 will typically be packaged in a conventional sterile packaging in a known manner for shipment. After a wire guide (not shown) has been positioned in a patient's body across a treatment location, the catheter 30 may be slid over the wire guide to position the distal carrier segment 32 and the attached self expanding stent 45 at the treatment location within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. After the distal carrier segment 32 is properly positioned and it is now time to deploy the self expanding stent 45, the user may depress pusher 85 to disengage lock 80 and move latch 81 out of contact with the radially outward thumb surface 66 of thumbwheel 65.

A method of operating vascular intervention device delivery system 10, 60 includes rotating the thumbwheel 15, 65 in a reverse direction to wind pull 38 onto spool 17, 67 to build up tension in the retractable sheath 37 and pull 38 without moving the retractable sheath 37 relative to the distal carrier segment 32 of catheter 30. During this step, wedge pin 25, 75 will remain in or move to its unwedged position, primarily responsive to interaction between the outer surface of the wedge pin 25, 75 with the curved wall 34. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel 15, 65 is paused, tension in the pull 38 and the retractable sheath 37 are maintained by holding the mechanism 20, 70 preventing rotation of the thumbwheel 15, 65 in the forward direction. Holding mechanism 20, 70 may be considered to be in a hold configuration when wedge pin 25, 75 moves or rolls to the wedged position jammed between curved wall 34 and planar wall 35. Those skilled in the art will appreciate that rotation of thumbwheel 15, 65 in the reverse direction dislodges wedge pin 25, 75 from its wedged position to its unwedged position, primarily responsive to wedge pin 25, 75 rolling interaction with curved wall 34. A remaining portion of the distal carrier segment 32 is then uncovered to facilitate complete deployment of the self expanding stent 45 by resuming rotation of the thumbwheel 15, 65 in the reverse direction until retractable sheath 37 arrives at its second position fully uncovering distal carrier segment 32.

During deployment, when thumbwheel 15, 65 is being rotated in the reverse direction, one could expect wedge pin(s) 25, 75 to rotate about its own axis responsive thereto. In addition, the holding mechanism could be expected to orbit the rotation axis 14, 64 during the deployment procedure. As shown, holding mechanism 20, 70 may include a spring 24 to assist in biasing the wedge pin 25, 75 toward the wedged position to better insure that little to no rotation of thumbwheel 15, 65 occurs in the forward direction when the thumbwheel is released. In other words, wedge pin 25, 75 may find itself in its wedged position whenever thumbwheel 15, 65 is not being rotated.

An important aspect of the ratchet operated vascular intervention device delivery system 10, 60 of the present disclosure is to allow for rotation of thumbwheel 15, 65 in one direction only. This means that the pull 38 and hence the retractable sheath 37 can only be pulled proximally. If the thumbwheel 15, 65 were able to rotate in both directions, it could cause the pull 38 to slack and possibly jump out of the collection diameter of the spool 17, 67 on thumbwheel 15, 65. Also, by keeping the rotation of thumbwheel 15, 65 to one direction only, holding mechanism 20, 70 allows all of the energy already placed in the system 10, 60 by the user to be maintained. For example, if the user was to partially deploy a self expanding stent 45 that had a deployment force of 30 N they will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vascular intervention device delivery system comprising:
   a handle;
   a thumbwheel rotatably mounted in the handle and having a radially outward thumb surface;
   a holding mechanism operably positioned between the handle and the thumbwheel, and including a wedge pin trapped to move in a wedge shaped cavity, which is defined by the thumbwheel and the handle, between a wedged position at which the thumbwheel is prevented from rotating with respect to the handle in a forward direction, and a unwedged position at which the thumbwheel is permitted to rotate with respect to the handle in a reverse direction, and wherein the wedge pin moves between the wedged position and the unwedged position responsive to rotation of the thumbwheel;
   a catheter with a proximal end attached to the handle, and a distal carrier segment for mounting a vascular intervention device thereon;
   a retractable sheath movable from a first position covering the distal carrier segment to a second position retracted proximally uncovering the distal carrier segment; and
   a pull extending between the thumbwheel and the retractable sheath; and
   the retractable sheath moving responsive to rotation of the thumbwheel in the reverse direction.

2. The vascular intervention device delivery system of claim 1 wherein the holding mechanism includes a spring operably positioned to bias the wedge pin toward the wedged position.

3. The vascular intervention device delivery system of claim 2 wherein the thumbwheel is rotatable about a first axis;
   the wedge pin defines a second axis; and
   the wedge pin rotates about the second axis in the wedge shaped cavity responsive to rotation of the thumbwheel in the reverse direction about the first axis.

4. The vascular intervention device delivery system of claim 3 wherein the wedge shaped cavity includes a first wall and a second wall that converge; and
   the first wall being defined by one of the thumbwheel and a portion of the handle; and
   the second wall being defined by the other of the thumbwheel and the portion of the handle.

5. The vascular intervention device delivery system of claim 4 wherein the holding mechanism orbits the first axis responsive to rotation of the thumbwheel in the reverse direction.

6. The vascular intervention device delivery system of claim 5 wherein the first wall is planar; and
   the second wall is a curved portion of a cylindrical surface.

7. The vascular intervention device delivery system of claim 6 wherein the holding mechanism is a first holding mechanism;
   a second holding mechanism, which is identical to the first holding mechanism, operably positioned between the handle and the thumbwheel; and
   the first holding mechanism and the second holding mechanism being located on opposite sides of the first axis.

8. The vascular intervention device of claim 1 including a self expanding stent positioned radially between the retractable sheath and the distal carrier segment of the catheter.

9. The vascular intervention device delivery system of claim 8 wherein the holding mechanism orbits an axis responsive to rotation of the thumbwheel in the reverse direction about the axis;
   the wedge shaped cavity includes a planar wall defined by one of the thumbwheel and a portion of the handle that converges with a curved wall defined by the other of the thumbwheel and the portion of the handle.

10. The vascular intervention device delivery system of claim 9 wherein the holding mechanism includes a spring operably positioned to bias the wedge pin toward the wedged position.

11. The vascular intervention device delivery system of claim 1 including a lock movable between a locked position and an unlocked position;
    the lock includes a latch positioned in the handle and moveable along a line between the locked position at which the latch engages the radially outward thumb surface, and the unlocked position at which the latch is out of contact with the radially outward thumb surface; and
    a pusher at least partially positioned outside the handle and being operably coupled to move the latch from the locked position to the unlocked position.

12. The vascular intervention device delivery system of claim 11 wherein the pusher includes a surface that engages a post that is attached to the latch and oriented perpendicular to the line.

13. The vascular intervention device delivery system of claim 12 wherein the holding mechanism orbits an axis responsive to rotation of the thumbwheel in the reverse direction about the axis;
    the wedge shaped cavity includes a planar wall defined by one of the thumbwheel and a portion of the handle that converges with a curved wall defined by an other of the thumbwheel and the portion of the handle.

14. The vascular intervention device delivery system of claim 13 wherein the holding mechanism includes a spring operably positioned to bias the wedge pin toward the wedged position.

15. A method of operating a vascular intervention device delivery system that includes a thumbwheel rotatably mounted in the handle; a holding mechanism operably positioned between the handle and the thumbwheel, and including a wedge pin trapped to move in a wedge shaped cavity, which is defined by the thumbwheel and the handle, between a wedged position at which the thumbwheel is prevented from rotating with respect to the handle in a forward direction, and an unwedged position at which the thumbwheel is permitted to rotate with respect to the handle in a reverse direction, and wherein the wedge pin moves between the wedged position and the unwedged position responsive to rotation of the thumbwheel; a catheter with a proximal end attached to the handle, and a distal carrier segment for mounting a vascular intervention device thereon; a retractable sheath movable from a first position covering the distal carrier segment to a second position retracted proximally uncovering the distal carrier segment; a pull extending between the thumbwheel and the retractable sheath, and the retractable sheath moving responsive to rotation of the thumbwheel in a reverse direction, and the method comprising the steps of:

- rotating the thumbwheel in the reverse direction to build up tension in the retractable sheath and pull without moving the retractable sheath relative to the distal carrier segment of the catheter;
- uncovering a portion, which is less than all, of the distal carrier segment by continuing to rotate the thumbwheel in the reverse direction;
- pausing rotation of the thumbwheel in the reverse direction;
- maintaining tension in the pull and the retractable sheath by moving the wedge pin of the holding mechanism to the wedged position and preventing rotation of the thumbwheel in the forward direction; and
- uncovering a remaining portion of the distal carrier segment by resuming rotation of the thumbwheel in the reverse direction and moving the wedge pin of the holding mechanism to the unwedged position.

16. The method of claim 15 wherein the step of moving the wedge pin to the wedged position is performed at least partially responsive to a force from a spring.

17. The method of claim 16 wherein the holding mechanism orbits an axis responsive to rotation of the thumbwheel in the reverse direction about the axis.

18. The method of claim 17 wherein the axis is a first axis; the wedge pin defines a second axis; and
the wedge pin rolls about the second axis responsive to rotation of the thumbwheel in the reverse direction about the first axis.

19. The method of claim 15 including a step of enabling operation of the thumbwheel by moving a lock from a locked position to an unlocked position.

20. The method of claim 19 wherein the step of moving a lock includes pushing a pusher to move a latch from engagement with the radially outward thumb surface to being out of contact with the radially outward thumb surface.

* * * * *